US006567682B1

(12) United States Patent
Osterweil et al.

(10) Patent No.: US 6,567,682 B1
(45) Date of Patent: May 20, 2003

(54) APPARATUS AND METHOD FOR LESION FEATURE IDENTIFICATION AND CHARACTERIZATION

(75) Inventors: Josef Osterweil, Rockville, MD (US); Niels K. Winsor, Albuquerque, NM (US)

(73) Assignee: Carecord Technologies, Inc., Rockville, MD (US)

( * ) Notice: Subject to any disclaimer, the term of this patent is extended or adjusted under 35 U.S.C. 154(b) by 99 days.

(21) Appl. No.: 09/711,966

(22) Filed: Nov. 15, 2000

Related U.S. Application Data (60) Provisional application No. 60/165,754, filed on Nov. 16, 1999.

(51) Int. Cl.[7] .................................................. A61B 5/05
(52) U.S. Cl. ........................ 600/407; 348/77; 382/154
(58) Field of Search ................................ 600/407, 476; 128/920, 922; 356/397; 348/77; 382/154, 291

(56) References Cited

U.S. PATENT DOCUMENTS

| | | | | |
|---|---|---|---|---|
| 5,080,100 A | * | 1/1992 | Trotel | 348/77 |
| 5,519,208 A | * | 5/1996 | Esparza et al. | 250/226 |
| 5,648,915 A | * | 7/1997 | McKinney et al. | 382/141 |
| 5,689,575 A | * | 11/1997 | Sako et al. | 382/118 |
| 6,032,070 A | * | 2/2000 | Flock et al. | 600/310 |
| 6,081,739 A | * | 6/2000 | Lemchen | 600/407 |
| 2002/0044682 A1 | * | 4/2002 | Weil et al. | 382/154 |

OTHER PUBLICATIONS

Pp. 168 through 171 of *Vector Analaysis With An Introduction To Tensor Analysis*, by A.P. Wills (Dover Publications, Inc., 1931, 1958.
Pp. 655 through 659 of *Methods Of Theoretical Physics*, by Morse et al. (McGraw–Hill Book Company, Inc., 1953).

* cited by examiner

*Primary Examiner*—Henry C. Yuen
*Assistant Examiner*—Mahmoud Gimie (57) ABSTRACT

An apparatus and method for determining a characteristic of a selected skin lesion. A capture device produces data representing an image of an object. A processing device processes the data to derive a three-dimensional model of the skin lesion, which is stored in a database. A reporting device indicates at least one specific property of the selected skin lesion. The processing device determines a change in at least one specific property of the skin lesion by comparing the three-dimensional model with at least one previously derived three-dimensional model that is stored in the database.

31 Claims, 7 Drawing Sheets

APPARATUS AND METHOD FOR LESION FEATURE IDENTIFICATION AND CHARACTERIZATION

CROSS-REFERENCE TO RELATED APPLICATIONS

The present application claims the benefit under 35 U.S.C. §119(e) of U.S. Provisional Application No. 60/165,754, filed on Nov. 16, 1999, the disclosure of which is expressly incorporated by reference herein in their entirety.

FIELD OF THE INVENTION

The present invention is directed to an apparatus and method for determining the severity of pressure sores, such as, for example, wounds or ulcers associated with an individual, and to assess the rate at which such wounds heal. The present invention relates more specifically to an optical apparatus and a method for using the optical apparatus that enables medical personal to accurately measure an effectiveness of a given pressure sore treatment.

BACKGROUND AND RELATED INFORMATION

Individuals that are immobile, such as, for example, individuals confined to a bed for an extended period of time, have a tendency to develop pressure sores (or ulcers). Pressure ulcers, commonly referred to as bed sores or pressure sores, are areas of local tissue trauma with a skin defect in the superficial (e.g., epidermis) or deeper (e.g., dermis) layers of the skin. Such sores usually develop where soft tissue is compressed between bony prominences and external surfaces for a prolonged period of time, and can extend into layers deeper than the skin (e.g., subcutaneous layer). Pressure sores are often painful and slow to heal.

Procedures for treating bed sores vary in effectiveness and cost. Although cost is an important consideration in selecting a course of treatment, the treatment that is chosen may also depend upon other factors, such as, but not limited to, the nutritional and general health status of the patient (individual). Further, since each individual reacts to treatments differently, a treatment that is effective for one patient may be ineffective (or less effective) for another patient.

Typically, the effectiveness of a selected treatment is determined by manually examining the bed sore. For example, an approximation of the severity of the bed sore may be determined by measuring the length and width using a mechanical measuring device, after which, a subjective estimation of the depth of the ulcer is made. By repeating this examination over a period of time, and comparing the measured results, it is possible to determine the degree of healing (or lack of healing) of the wound. Unfortunately, such a procedure is very labor intensive, and requires that the examination and measurements be performed by skilled personnel. Further, such measurements are inaccurate, and require long periods of time (e.g., such as, for example, several days) between measurements to determine whether the selected treatment is effective or should be changed.

SUMMARY OF THE INVENTION

Accordingly, an object of the present invention is directed to an apparatus and method that quickly and accurately determines the effective of a treatment selected for healing a bed sore. The apparatus is easily operated by an individual, such as a technician, certified nurse assistant, or other non-medical personal. The apparatus measures and/or characerizes a selected skin lesion, and has a capture device that produces data representing an image of an object; a processing device that processes the data to derive a three-dimensional model of the skin lesion, which is stored in a database; and a reporting device, such as, for example, a display, that indicates at least one specific property of the selected skin lesion, wherein the processing device determines a change in at least one specific property by comparing the three-dimensional model with at least one previously derived three-dimensional model stored in the database.

According to an advantage of the invention, the capture device includes, for example, an electronic stereoscopic camera, an electronic camera having at least two periscopes, plural cameras, an electronic camera that captures at least two images on a split frame, a scanner, or any other capture device that captures space diverse views of the object.

According to a feature of the invention, the capture device includes a memory to stores the captured image. Accordingly, the stored captured image may be analyzed by the processing device at a time that is substantially later from when the image was captured. In this regard, the apparatus includes an interface that selectively connects the capture device to the processing device.

According to another feature of the invention, the data representing an image includes information related to at least one of color, and texture of the object. This data may be stored in the database and is correlated with a selected information, such as, for example, at least one of patient identification, lesion location, the date the data representing the image of the object was produced, the time the data representing the image of the object was produced, and identification of personnel treating the object.

A still further feature of the invention is the inclusion of a pattern generator that projects a predetermined pattern onto the object. The predetermined pattern projected by the pattern generator may be, for example, a grid pattern, or a plurality of geometric shapes.

According to another object of the invention, a method is disclosed for measuring and/or characterizing a selected skin lesion. The method produces data that represents an image of an object; processes the data to derive a three-dimensional model of the skin lesion, which is stored in a database; and indicates at least one specific property of the selected skin lesion, wherein a change in the at least one specific property is determined by comparing the three-dimensional model with at least one previously derived three-dimensional model stored in the database.

According to an advantage of this method, an electronic stereoscopic camera, an electronic camera having at least two periscopes to capture the image, multiple cameras, a camera that captures at least two images on a split frame, a scanner, or any capture device that captures space diverse views of the object may be used to capture the image.

The captured image may be stored in a memory, so that, for example, it can be processed at a time that is substantially later from when the image was captured, and/or at a location remote from where the image was captured.

According to a still further object of the invention, a method is disclosed for characterizing features of an object, in which an initial image view is transformed to a two-dimensional physical perspective representation of an image corresponding to the object; unique features of the two-dimensional perspective representation of the image are identified; the identified unique features are correlated to produce a three-dimensional physical representation of all uniquely-identified features; and three-dimensional characteristic features of the object are determined.

A still further object of the invention comprises an apparatus for measuring and/or characterizing features of an object, comprising an imaging device that capture a two-dimensional image of the object, a processing device that processes the captured image to produce a three-dimensional representation of the object, in which the three-dimensional representation includes parameters indicating a predetermined feature of the object; a database that stores the parameters; a comparing device that compares the stored parameters to previously stored parameters related to the object to determine a change in the three-dimensional representation of the object; and a reporting device that uses results of the comparison by the comparing device to generate a report pertaining to a change in the object.

BRIEF DESCRIPTION OF THE DRAWINGS

The foregoing and other objects, features and advantages of the invention will be apparent from the following more particular description of preferred embodiments, as illustrated in the accompanying drawings which are presented as a non-limiting example, in which reference characters refer to the same parts throughout the various views, and wherein.

DETAILED DISCLOSURE OF THE INVENTION

The particulars shown herein are by way of example and for purposes of illustrative discussion of embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the present invention may be embodied in practice.

According to the present invention, an image of an area of interest (e.g., pressure sore) is obtained, and the image is processed to determine features of the ulcer (pressure sore).

Figure 1:
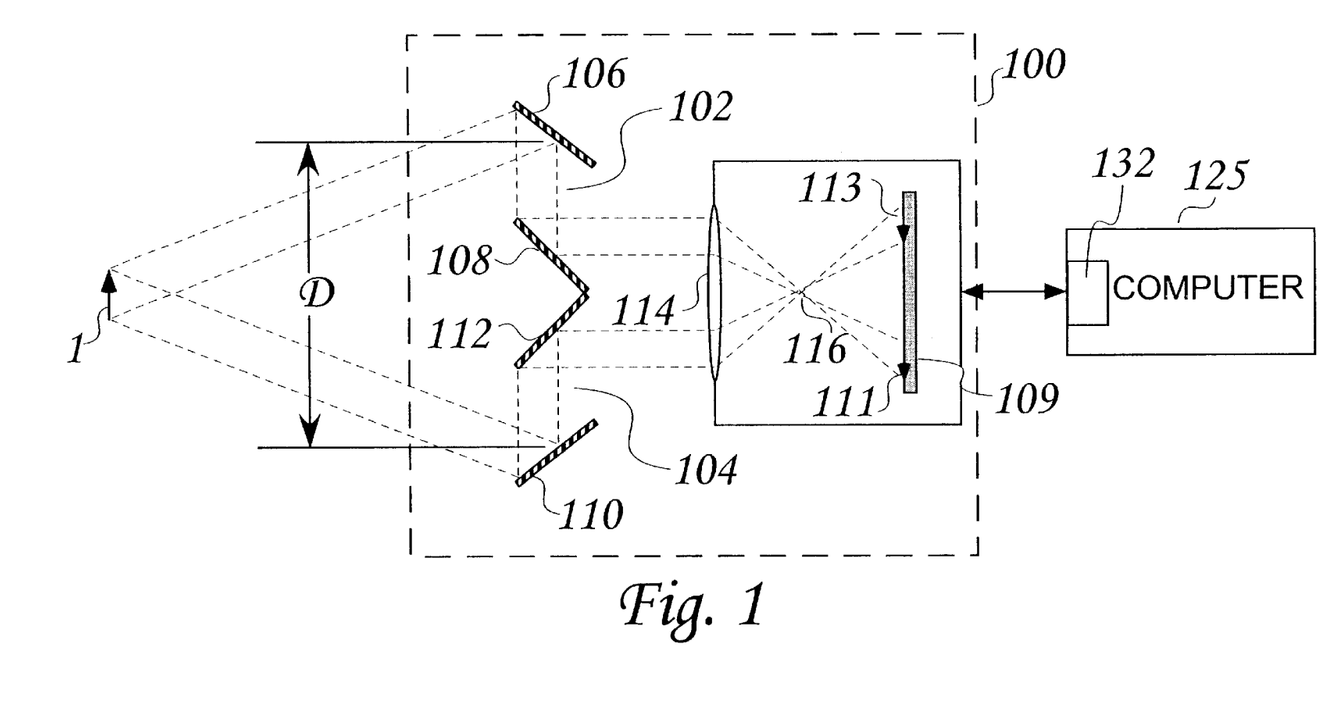
FIG. 1 illustrates a first embodiment of an apparatus for analyzing the effectiveness of a pressure sore treatment.

FIG. 1 illustrates an embodiment of the current invention. As shown in FIG. 1, a stereoscopic camera (capture device) 100, such as, but not limited to an electronic or digital camera, is employed to capture space diverse views of an object, such as, but not limited to, for example, a pressure sore 1 on an individual. In the disclosed embodiment, the camera 100 includes an upper periscope 102 and a lower periscope 104. In this regard, while a limited number of camera setups will be described herein, it is understood that other (non-disclosed) setups may be equally acceptable and are not precluded by the present invention.

Further, while the disclosed embodiment utilizes a single camera having two (or more) periscopes for capturing two (or more) images on a split frame, it is understood that a similar effect can be obtained by a camera that has one periscope to capture one image on one-half of the fame and a second image that is directly captured by the camera on a second-half of the frame.

Preferably, camera 100 is moved a precise distance, generally in a parallel plane to the plane of the ulcer 1, to collect stereoscopic information. It is noted that a single camera traveling along a rail and capturing multiple images, each at a predetermined segment of travel (akin to synthetic aperture radar swath), will provide information about the ulcer 1 in great detail.

The upper periscope 102 comprises an outer mirror 106 and an inner mirror 108 that direct a first light ray received from the object 1 towards a first location of a focal plane of the camera 100, where, for example, a sensor 109 is positioned to detect a first image 111. Similarly, the lower periscope 104 comprises an outer mirror 110 and an inner mirror 112 that direct a second light ray received from the object 1 towards a second location of the focal plane of the camera 100 where the sensor 109 is positioned to detect a second image 113.

In the disclosed embodiment, the sensor 109 comprises a charge couple device (CCD) sensor. Such sensors are well know to those skilled in the art, and thus, a discussion of their construction is omitted herein. In the disclosed embodiments, the CCD sensor comprises, for example, a two-dimensional scanning line sensor or matrix sensor. However, it is understood that other types of sensors may be employed without departing from the scope and/or spirit of the instant invention. In addition, it is understood that the present invention is not limited to the particular camera construction or type described herein. For example, a digital still camera, a video camera, a camcorder, or any other electrical, optical, acoustical or chemical recording means that records (collects) the required information for subsequent processing may be used. In this regard, digital cameras have the advantage of capturing images that are immediately ready for processing, whereas, for example, a film camera requires development of the film and scanning of the image recorded by the film before processing can begin.

Further, it is understood that the image (or images) captured by the camera can be processed (to be described) substantially "in real time" (e.g., at the time of capturing the image(s)), or stored in, for example, a memory, for processing at a later time and/or at a location remote from the camera, without departing from the spirit and/or scope of the invention.

A location of the outer mirrors 106 and 110 relative to the object 1, and in particular, a distance D between the outer mirrors 106 and 110 determines the effectiveness of a stereoscopic analysis of the object 1. The outer mirrors 106 and 110 operate to reflect light rays arriving from the object (pressure sore) 1 towards the inner mirrors 108 and 112. The inner mirrors 108 and 112 operate to reflect the light rays toward a lens 114 of the camera 100. For purpose of illustration, dotted lines in FIG. 1 depict the optical path of the light rays from object 1 to the first and second locations on the sensor 109. Since the upper and lower periscopes 102 and 104 provide for the capturing of a stereoscope image, two distinct images fall upon the camera lens 114. The light rays pass through the camera lens 114, converge at a focus point 116 and eventually impinge the focal plane of the camera 100 where the sensor 109 is positioned.

Note that the two images 111 and 113 are inverted with respect to the object 1. It is further noted that in place of the camera 100 and periscopes 102 and 104, two cameras may be used without departing from the scope and/or spirit of the present invention. In such a situation, each camera may be positioned, for example, at the locations depicted by the outer mirrors 106 and 110 in FIG. 1, so that a lens associated with each camera is spaced apart by the distance D. In this setup, each camera has its own sensor to capture an image. This differs from the embodiment shown in FIG. 1, in which the periscopes 102 and 104 operate to deliver two images to a single image frame.

Each image captured by the camera 100 (by the single sensor when the two periscopes are employed, or by the two sensors when two cameras are used) are converted to electrical signals having a format that can be utilized by an appropriate image processing device (e.g., a computer 125 executing an appropriate image processing routine), so as to, for example, process the captured image, analyze data associated with the captured image, and produce a report related to the analysis.

Figure 2A:
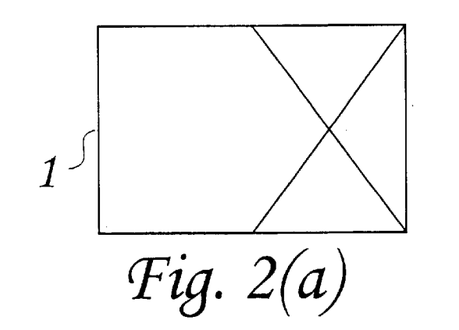
FIGS. 2(a) to 2(g) illustrate optical image transformations produced by the invention of FIG. 1.

FIGS. 2(a) to 2(g) illustrate optical image transformations produced by the stereoscopic camera 100 of FIG. 1, as well as initial image normalization in the electronic domain. In FIG. 2(a), object (pressure sore) 1 is illustrated as a rectangle with an "X" marking its right half. The marking helps in recognizing the orientation of images. Object 1 is in a parallel plane to the camera's focal plane, and faces the camera of FIG. 1. For convenience, the following discussion of FIGS. 2(b) to 2(g) will refer to "right" and "left", instead of "upper" and "lower" as was the case in FIG. 1. However, it is understood that use of the terminology such as, for example, "left", right", "upper" and "lower" is simply used to differentiate between plural images produced by the stereoscopic camera 100.

Figure 2B:
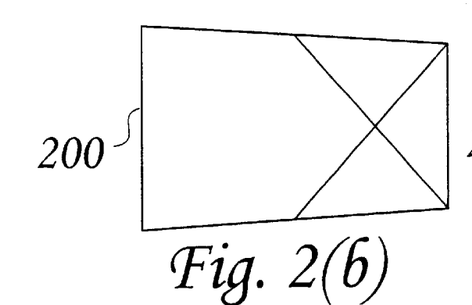

FIG. 2(b) represents an image 200 of the object 1 as seen through a left periscope section (corresponding to, for example, upper periscope 102 of the stereoscopic camera 100 in FIG. 1), showing a perspective distortion (e.g., trapezoidal distortion) of the image and maintaining the same orientation ("X" marking on the right half as on the object 1 itself).

Figure 2C:
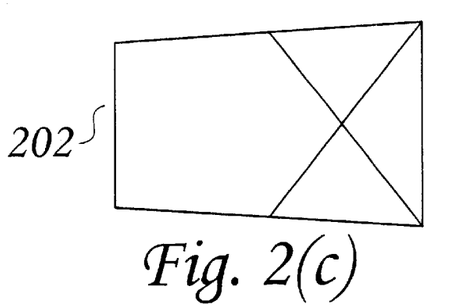

FIG. 2(c) represents an image 202 of the object 1 as seen through a right periscope section (corresponding to, for example, the lower periscope of the stereoscopic camera 100 in FIG. 1) showing a perspective distortion (e.g., trapezoidal distortion) and maintaining the original orientation ("X" marking on the right half as on the object 1 itself).

Figure 2D:
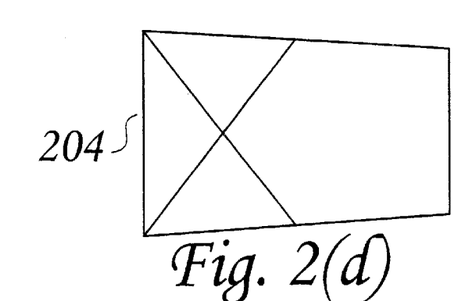

FIG. 2(d) represents an image 204 of an object projection on the left side of the camera's focal plane sensor 109 through the right periscope section. As shown in FIG. 2(d), the orientation of image 204 is inverted (e.g., the "X" marking is located on the left side), but the perspective distortion is maintained. It is noted that image 202 on the right side (FIG. 2(c)) arrived as image 204 on the left side.

Figure 2E:
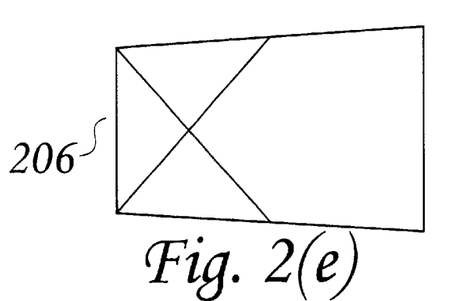

Similarly, image 206 (FIG. 2(e)) illustrates the object projection on the right side of the camera's focal plane sensor 109 through the left periscope section. Image 206 has been inverted (e.g., the "X" marking is located on the left side), but the perspective distortion is maintained. Also note that image 200 on the left side arrived as image 206 on the right side.

It is noted that in addition to the perspective distortion, additional distortions (not illustrated) may additionally occur as a result of, but not limited to, for example, a misalignment of the optical elements, and/or an imperfection in the optical elements, and/or an imperfection in the camera's sensor 109. The images 204 and 206 must be restored to minimize the distortion effects within the resolution capabilities of the camera's sensor 109. The image restoration is done in the electronic and software domains by the computer 125.

According to the present invention, a database is employed to maintain a record of the distortion shift for each pixel of the sensor 109. This database is created at the time of manufacture of the camera 100, when the camera is initially calibrated, and is updated each time periodic maintenance of the camera 100 is performed. The information stored in the database is used to perform a restoration process of the two images, as will be described below. This database may be stored, for example, in the computer 125 used with the camera 100, or in a memory of the camera 100.

Figure 2F:
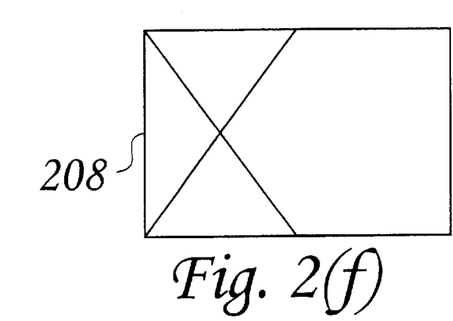

Image 208 in FIG. 2(f) represents a restored version of image 204, derived from the left side of the camera's focal plane sensor 109, which includes a correction for the above-noted perspective distortion. Similarly, image 210 in FIG. 2(g) represents a restored version of image 206, derived from the right side of the camera's focal plane sensor 109, which includes a correction for the above-noted perspective distortion.

Figure 3:
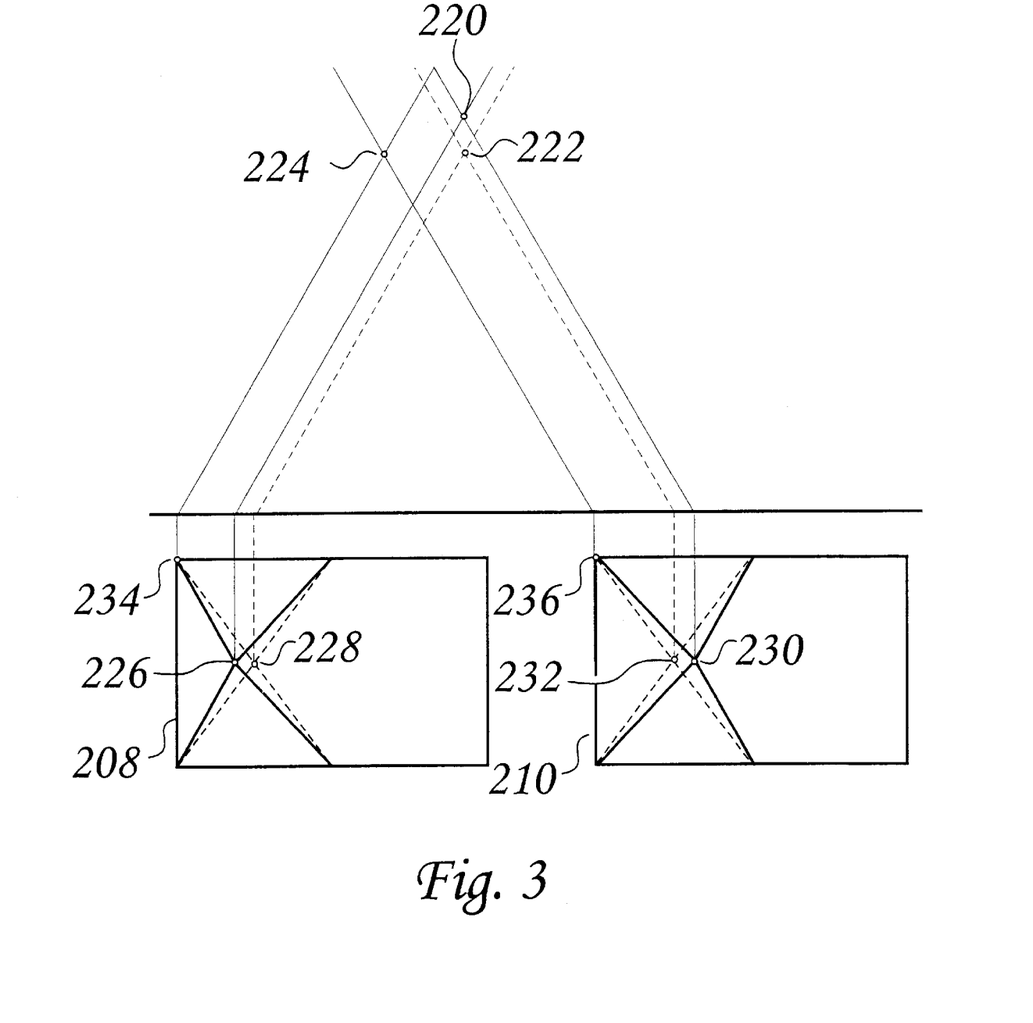
FIG. 3 illustrates a three-dimensional mapping performed by the invention of FIG. 1.

FIG. 3 illustrates a stereoscopic process for three-dimensional mapping. Pressure sores generally have an irregular, three-dimensional shape. In order to simplify the following discussion, an explanation is set forth with respect to three points of a concave pyramid (not shown); a tip 220 of the pyramid, a projection 222 of the tip 220 on a base of the pyramid perpendicular to the base, and a corner 224 of the base of the pyramid. The tip 220 points away from the camera (not shown), while the base is in a plane parallel to the focal plane of the camera.

Figure 2G:
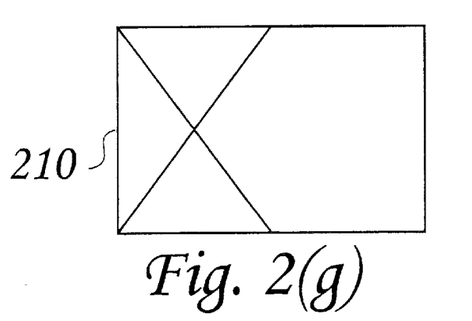

Flat image 208 of FIG. 2(f) and flat image 210 of FIG. 2(g) are shown in FIG. 3 by dotted lines for the object, described earlier, and by solid lines for the stereoscopic images of the three-dimensional object that includes the pyramid. FIG. 3 illustrates the geometrical relationship between the stereoscopic images 208 and 210 of the pyramid and the three-dimensional pyramid defined by the tip 220, its projection 222 on the base, and the corner 224 of the base. It is noted that a first image point 226 corresponding to tip 220 of the pyramid is shifted with respect to a left 228 of the flat object corresponding to the projection 222 of the tip 220. Similarly, a second image point 230 corresponding to the tip 220 of the pyramid is shifted with respect to a right 232 of the flat object corresponding to the projection 222 of the tip 220. The image points 234 and 236 corresponding to the corner 224 of the base of the pyramid are not shifted because the corner is part of the pyramid's base and in a plane, parallel to the focal plane of the camera, as is the flat object.

The first point 222 of the tip 220 on the base is derived as a cross-section between lines starting at projected points 228 and 232, and is inclined at an angle, as viewed by the outer mirror 106 of the upper periscope 102 and outer mirror 110 of the lower periscope 104. In the same manner, the tip 220 is determined from points 226 and 230, whereas a corner point 224 is derived from points 234 and 236. Note that points 224 and 222 are on a horizontal line that represent a plane of the pyramid base. It is further noted that point 220 is above the horizontal line, indicating a location outside the pyramid base plane on a distant side relative to the camera. The process of mapping the three-dimensional object is performed in accordance with rules implemented by a computer algorithm executed by the computer 125.

Figure 4:
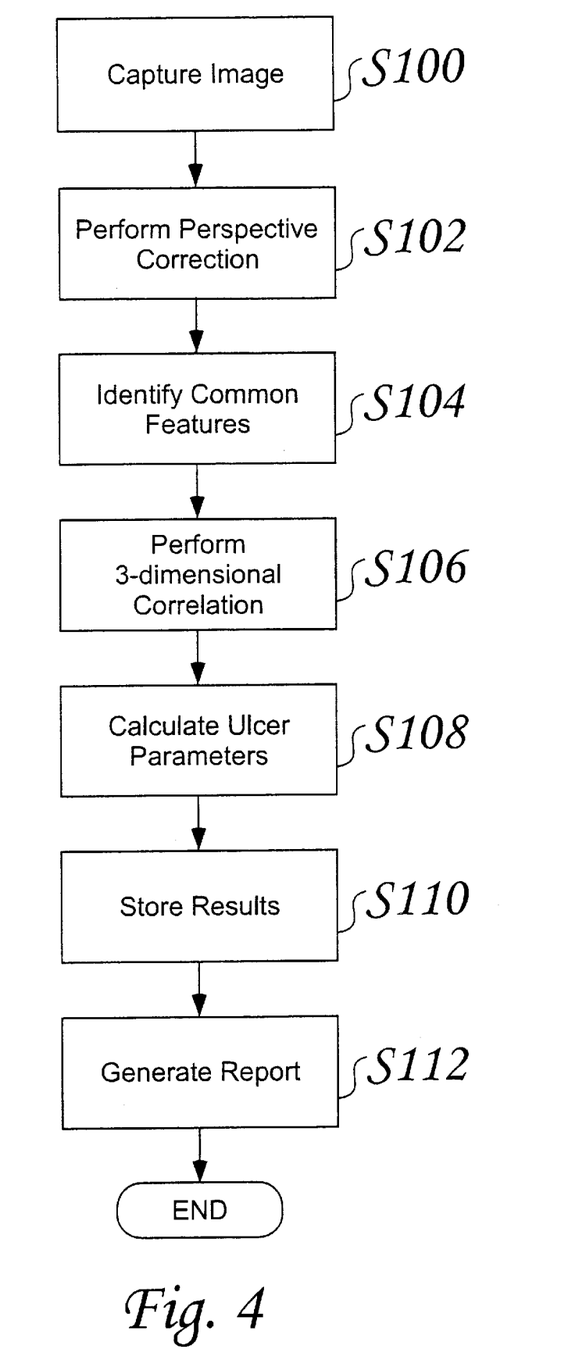
FIG. 4 illustrates a flowchart of data capturing and analyzing operations performed by the invention of FIG. 1.

FIG. 4 illustrates example operations performed by the computer 125. The computer 125 employed with the present invention comprises, for example, a personal computer based on an Intel microprocessor, such as, for example, a Pentium III microprocessor (or compatible processor, such as, for example, an Athlon processor manufactured by AMD), and utilizes the Windows operating system produced by Microsoft Corporation. However, it is understood that computers utilizing alternative processors and operating systems, such as, but not limited to, for example, an Apple Computer or a Sun computer, may be used without departing from the scope and/or spirit of the invention. It is understood that the operations depicted in FIG. 4 function to derive a three-dimensional (3D) model of the ulcer and its surroundings. Extrapolation of the surroundings provide an estimate of the 3D location of the healed skin in the absence of the ulcer. The volume between the estimated undisturbed skin and the actual surface of the ulcer yields a quantitative estimate of the amount of skin and/or other tissue that must be grown during the healing process to restore the skin to its normal healthy condition.

Figure 8:
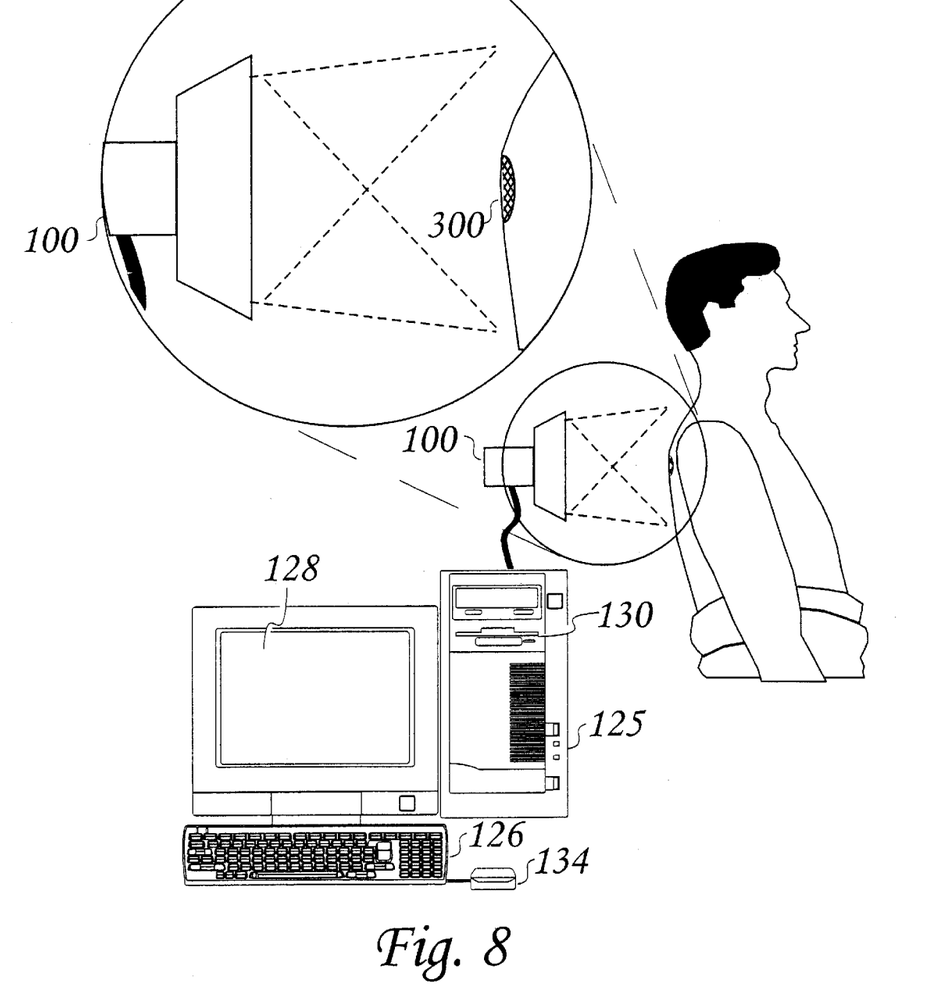
FIG. 8 illustrates a typical system configuration of the apparatus for analyzing pressure sores according to the present invention.

As shown in FIG. 8, computer 125 includes a keyboard 126, a monitor 128, a storage device, such as a hard drive (not shown), a removable drive 130, such as, for example, a zip drive or conventional 1.44 MB floppy disk drive, and a circuit board containing a processor, RAM, ROM, a video card, and input/output devices. It is noted that all the functions of the computer may be integrated into a single circuit board, or it may comprise a plurality of daughter boards that interface to a motherboard. While the present invention discloses the use of a conventional personal computer that is "customized" to perform the tasks of the present invention, it is understood that alternative processing devices, such as, for example, programmed logic array designed to perform the functions of the present invention, may be substituted without departing from the spirit and/or scope of the invention.

The computer 125 includes a frame capture device 132 that interfaces with the camera 100 of FIG. 1. Digital data representing the image captured by the camera 100 is transferred, via, for example, a USB or IEEE 1394 interface to the frame capture device 132 associated with the computer 125 by an appropriate cable (for example, a USB cable or IEEE 1394 cable) that also functions to selectively connect the camera 100 to the computer 125, for storage in a frame capture buffer that represents the image in rasterized form, such as, but not limited to, for example, a 640×480 bitmap image having a 24 bit color resolution. It is noted that when the cable is disconnected from the camera 100, the camera 100 may be used to capture images at a location remote from the computer 125, and/or to capture images that are processed by the computer 125 at a later time.

One skilled in the art recognizes that other methods of storage, with fewer or more "lines" of horizontal and vertical resolution, and fewer or more bits of color information, or simply gray-scale information, may be used without departing from the scope and/or spirit of the present invention. Further, it is recognized that if a conventional film camera is employed in place of an electronic imaging device, the image formed on the film is processed to produce a latent image, which may then be digitized using, for example, a scanner. The digitized data is then input to the frame capture buffer of the frame capture device 132.

The operations performed by the computer 125 will now be described with reference to FIG. 4. At step S100, an initial image view $C^{i,j}$ captured by the camera 100 is processed to obtain a two-dimensional physical perspective representation. The two-dimensional "physical" perspective representation of the left and right images is transformed (step S102) via a general metric transformation, $$P^{i,j} = \sum_{k=1}^{N_X} \sum_{l=1}^{N_Y} g_{k,l}^{i,j} C^{k,l} + h^{i,j}$$

to the "physical" image $P^{i,j}$.

In the disclosed embodiment, I and k are indices that range from 1 to $N_x$, where $N_x$ is the number of pixels in a horizontal direction, and j and 1 are indices that range from 1 to $N_y$, where $N_y$ is the number of pixels in a vertical direction. The transformation from the image view $C^{i,j}$ to the physical image $P^{i,j}$ is a linear transformation governed by $g_{k,l}^{i,j}$, which represents both a rotation and a dilation of the image view $C^{i,j}$, and $h^{i,j}$, which represents a displacement of the image view $C^{i,j}$.

It is recognized that these parameters differ for the left and right halves of a stereo pair. The parameters may be, for example, determined by placing a calibration screen with measured markings a predetermined distance in front of the device to determine parameters (coefficients) of the transformation. Further, one skilled in the art recognizes that there are more general (nonlinear) transformations that will accomplish this purpose, and maximize the accuracy in the transformation of the image, even in the presence of, for example, a distortion in, for example, the lenses, mirrors and/or windows.

In the linear case, the system is calibrated by placing a quantitative target, such as, for example, a graph or quadrille paper a measured distance from the system. In the non-linear case, it is necessary to place the target, and record its image, at a number of distances that span the volume in which measurements are to be taken. While the present invention describes a specific calibration technique, it is understood that variations may be made therein without departing from the spirit and/or scope of the invention.

The perspective image comprises a representation in physical space (measured in, for example, inches, meters or equivalent units of measure) of the actual physical location of the subject matter, as viewed in the two images. The metric coefficients $g_{k,l}^{i,j}$ and $h^{i,j}$ are derived from three (or more) physical features simultaneously identified in both images, as follows: from FIG. 1, the transformation from each field of view to a physical image is known. However, it is not known how far the observed object field is from the camera. When a physical feature, such as, for example, a naturally occurring feature on the skin, or an artificially-created feature (such as, for example, the intersection of two projected curves of light) is observed in two (or more) views, the distance from the camera(s) to the object can be determined. Once three such objects are identified, they uniquely determine a physical "field plane" relative to which the three-dimensional positions of all subsequently-correlated image locations can be determined.

In step S104, all pixels in the left and right images are examined to determine which features are common in both images for a three-dimensional correlation to be performed in step S106. It is noted that if the image data includes a significant amount of "noise", spline fits or other smoothing curves may be applied to the data, so that the fitted location of these curves is determined with a resolution greater than the pixel size.

Further, the computer 125 may include spline fit algorithms or equivalent numerical fitting of curves to the measured and interpolated surfaces, which are used to construct surface models of the boundary of the ulcer and of the volume of the ulcer. This provides the operator with the option of superimposing selected models of the same ulcer for detailed healing assessments. The operator can then determine which sub-regions in the ulcer may need additional attention.

In step S106, the three-dimensional correlation is performed on all observed features which are uniquely identified in both images. That is, if $L^{i,j}$ and $R^{i,j}$ are defined as the left and right physical images of the subject under study, respectively, then $$p^{k,l,m} = f^{k,l,m}(L,R)$$

is the three-dimensional physical representation of all uniquely-identified points. The transformation function $f$ is derived by using the physical transformation from step S102 and the physical geometry of the stereo image representation from step S104 to determine the distance from the camera to the observed field point pairs (e.g., one point in each image) using the physical coordinate geometry.

It is noted that in both the projected curves and the physical features, such as, for example, an edge of an ulcer, there are recognizable curves which do not have specifically-identifiable points. Consequently, artificial "points" are equally spaced along each such curve between the identified points. The artificial points are then correlated between the two images of the stereo pair. This is not a linear transformation, since it requires differencing perspective coordinates and extracting square roots to locate correlated points in three-dimensional physical space relative to the physical object plane.

In step S108, the physical representation obtained from step S106 is used (along with optional color information and/or optional contrast change information in the image) to determine where each ulcer is located in the three-dimensional image. For each ulcer, two three-dimensional fits are performed. The first three-dimensional fit comprises, but is not limited to, for example, a three-dimensional fit to the exterior of the ulcer, using, for example, smoothed curves to determine where the skin would be in the absence of the ulcer. The second three-dimensional fit comprises, but is not limited to, for example, a three-dimensional fit to the interior of the ulcer. The area of the ulcer is determined from the interior fit. The volume is defined as the volume included within the two fits, and the effective depth of the ulcer is simply the volume divided by the area. This has been found to be a more useful measure than the maximum separation between the two surfaces, since the separation at specific locations is subject to significant statistical error.

Step S110 stores the results of the measurements obtained in step S108 in, for example, a time progression form (e.g., database) that is relatively easy for a system user to extract for each patient. The data may be stored in, for example, the removable drive 130 of the computer 125, or a non-removable drive (not shown) of the computer. It is understood that the specific storage device and manner in which the data is stored is not critical to the success of the present invention, and thus, variations therein may exist without departing from the spirit and/or scope of the invention.

It is noted that the stored information specific to the patient may be obtained, for example, by an operator that manipulates a keyboard 126 of the computer 125. Alternatively, other methods or devices (such as, but not limited to, for example, a voice recognition system) may be used to retrieve the stored measurement results.

In step S112, the measurement results stored in the database are combined with pre-defined design and report structure information to produce a report that is output to, for example, the monitor 128 of the computer 125, so as to provide the system operator with information on the status of the ulcer(s). This information is presented for specific patients, so that the effectiveness of the current treatment can be evaluated. If multiple patients are using the same treatment, the statistical effectiveness of the treatment averaged over all these patients can be determined.

It is understood that the present invention is not limited to outputting the report to the monitor 128. Alternative output devices, such as, but not limited to, for example, a printer, may be used without departing from the scope and/or spirit of the invention.

The processed image information and its derived parameters regarding ulcer area and ulcer crater depth (which are relevant for determining the effectiveness of the treatment) are stored in the database under, for example, the patient's name, with identification of the ulcer's location, date, and other relevant data. Generally, reports from the database will focus on numerical and graphic presentation of selected parameters as a function of time. However, additional parameters, such as, but not limited to, for example, distinguishing color and/or texture of various areas of the ulcer, may also be saved in the database for future retrieval and evaluation. For example, a notation in the database that the ulcer has a vivid red glossy color and has a granular texture implies growing cells, and thus, healing of the ulcer is in progress. On the other hand, a notation in the database that the ulcer exhibits a pale red or pink color may indicate a poor blood supply. Similarly, a notation in the database of a green yellow liquid discharge from the wound implies that a healing of the ulcer is about to begin, whereas a notation of a dark brown, non-shiny material indicates skin necrosis (death). Finally, it is noted that the image itself may be stored for later retrieval and two dimensional (or stereoscopic) viewing.

According to a refinement of the embodiment, the operator may retrieve data from the database in a form that permits him to study the history of a specific ulcer, as well as compare the performance of a treatment for similar ulcers on different patients.

Figure 5:
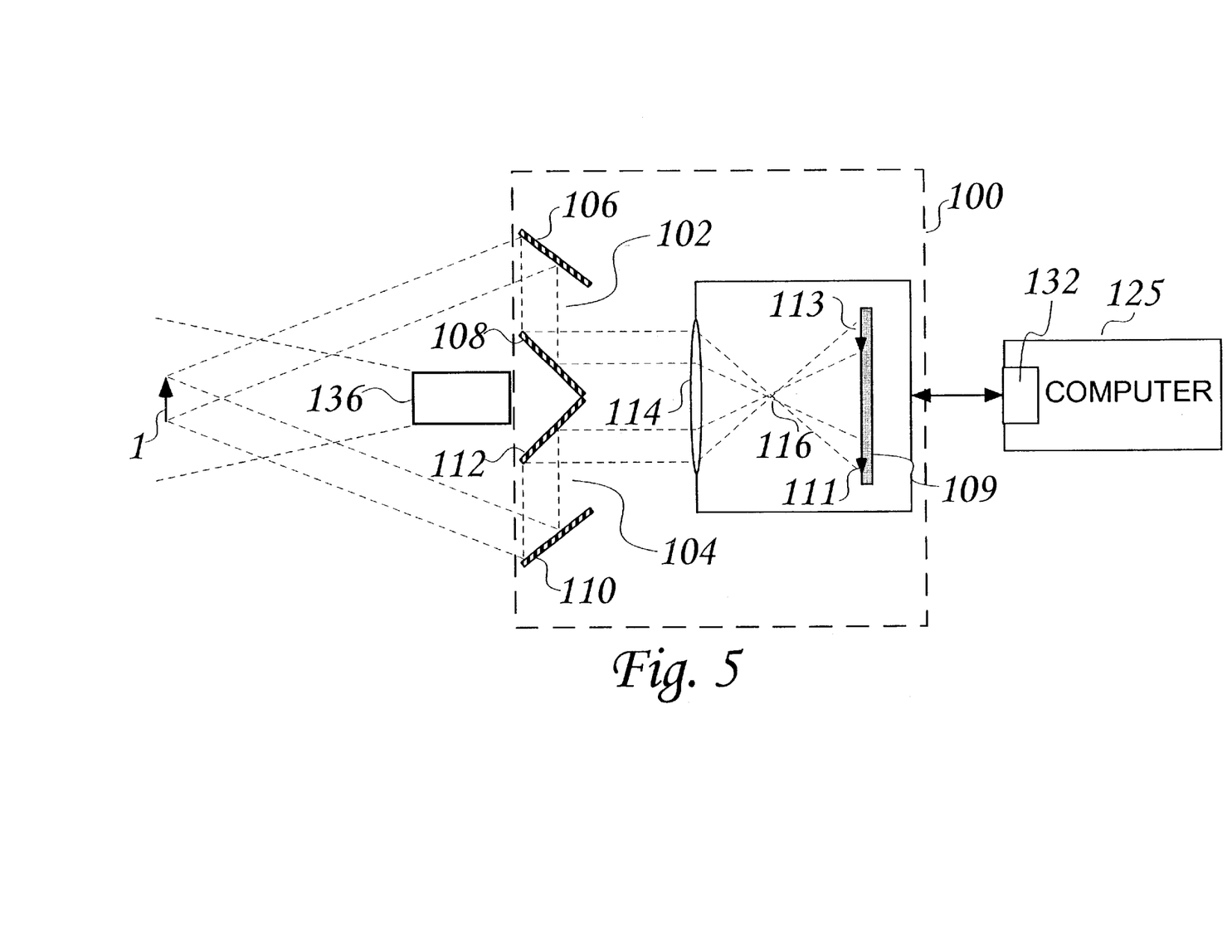
FIG. 5 illustrates a second embodiment of the present invention.

A second embodiment of the present invention is illustrated in FIG. 5. A discussion of the elements that are common to those in FIG. 1 is omitted herein; only those elements that are new will be described.

The second embodiment differs from the first embodiment shown in FIG. 1 by the inclusion of a pattern projector (generator) 136. The pattern projector 136 assists in the stereoscopic object analysis for the three-dimensional mapping of the object. Since the stereoscopic analysis and three-dimensional mapping of the object is based on a shift of each point of the object in the right and left images, it is important to identify each specific object point in both the right and left images. Most objects within categories listed for analysis (such as, but not limited to, for example, lesions, ulcers, scars, nevi, and actinic-keratoses) have a limited number, if any, of distinctly identifiable points. Providing the object with distinct markings provides the best references for analytical comparison of the position of each point in the right and left images, respectively. However, marking a pressure ulcer is not practical, as it may, for example, cause discomfort to the patient, and/or may cause further damage to the ulcer.

Accordingly, the second embodiment of the present invention employs the pattern generator 136 to project a pattern of light (or shadows) substantially perpendicular to the object that appear as distinct markings on the object. In the second embodiment, the pattern projector 136 is shown to illuminate the object 1 from a vantage position of the center of the camera. However, it is understood that the pattern generator may be located at different positions without departing from the scope and/or spirit of the invention.

The pattern generator 136 projects a stationary pattern of light onto the ulcer and its surroundings. The projected pattern may be visible or invisible (for example, infrared) light, so long as the camera can detect the image and/or pattern of light. It is noted that the projected pattern is especially useful when the ulcer or its surroundings are relatively featureless, making it difficult to construct a 3D representation of the ulcer volume.

Figure 6:
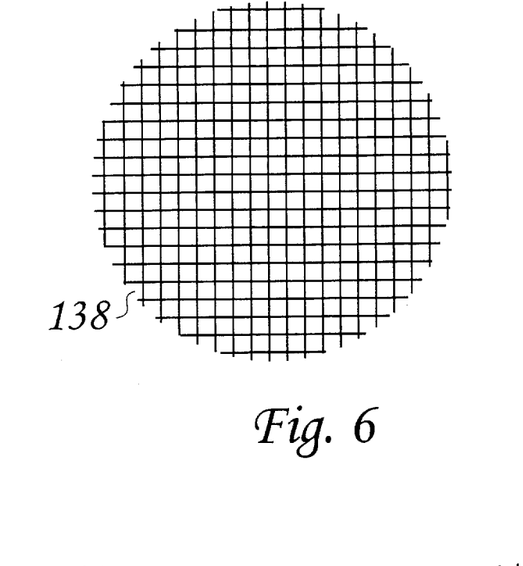
FIG. 6 illustrates a grid form pattern produced by a pattern generator used with the second embodiment of the invention.

FIG. 6 illustrates a grid form pattern 138 projected by the pattern projector 136. However, it is appreciated that alternative patterns may be utilized by the present invention without departing from the scope and/or spirit of the invention. For example, the pattern can vary from a plain quadrille grid or a dot pattern to more distinct marks, such as many different small geometrical shapes in an ordered or random pattern.

In the grid form pattern shown in FIG. 6, dark lines are created on an illuminated background. Alternately, if multiple sequences of camera-captured frames (while the object is motionless) are to be analyzed, a moving point of light, such as, for example, a laser scan pattern, can be utilized. In addition, a momentary illumination of the entire object can provide an overall frame of reference for the analyzed object.

Figures 7A, 7B:
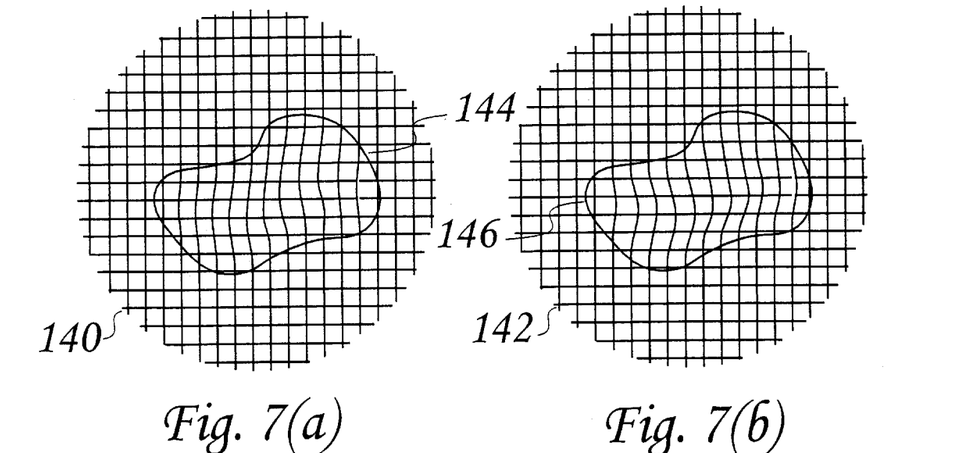
FIGS. 7(a) and 7(b) represent left and right images, respectively, that were imaged with the apparatus of the second embodiment.

FIG. 7(a) illustrates a left image 140, and FIG. 7(b) illustrates a right image 142 of an illuminated concave object (e.g., pressure ulcer) and a distortion 144 and 146 of the grid form pattern 138 on the left and right images 140 and 142, respectively. In particular, it is noted that the distortion 144 and 146 represents a gradual horizontal displacement of the grid form pattern to the left in the left image 140, and a gradual horizontal displacement of the grid form pattern to the right in the right image 142. A maximum horizontal displacement is noticeable close to the center of the ulcer, indicating the deepest section of the ulcer.

A variation of the second embodiment involves using a pattern generator that projects a dynamic (e.g., non-stationary) pattern, such as a raster scan onto the ulcer and its surroundings. This variation requires the use of a camera which has an image capture time that is short in comparison with the time during which the pattern changes, but which is long in comparison to the time required to once cover the region of interest with the pattern.

Another variation of the second embodiment is to use a pattern generator that projects uniquely-identifiable patterns, such as, but not limited to, for example, letters, numbers or geometric patterns, possibly in combination with a static or dynamic featureless pattern. This prevents the mislabeling of identification of intersections in stereo pairs, that is, incorrectly correlating an intersection in a stereo pair with one in a second photo of the pair, which is actually displaced one intersection along one of the grid lines.

FIG. 8 illustrates a typical system configuration using the stereoscopic camera 100 in conjunction with the computer 125 for image processing, deriving ulcer parameters, and reporting the measurement results. Camera 100 is aimed at an ulcer 300 located on a back of a patient. The operator manually aims the camera 100, by, for example, watching the image shown on the monitor 128. In the second embodiment, the pattern generator 136 may be utilized to project a grid form pattern onto the ulcer 300 in order to assist in the aiming of the camera.

The computer system 125 may optionally include a camera controller (not shown) that is interfaced with, for example, an electrically operated mount (not shown) to which the camera 100 is secured. The mount may then be instructed to move in three-dimensions (e.g., x, y and z coordinates) to control the positioning and/or operation of the camera 100. For example, the camera controller may be integrated into the computer 125, which is then interfaced with the mount via an electrical cable. A system operator of the computer 125 may then, for example, change a direction of movement of the camera, control artificial lighting used with the camera, and/or adjust controls which might be available in the camera and lighting hardware by inputting control commands via, for example, the keyboard 126, a mouse 134 or other input device. It is noted that the controls are generally adjusted to minimize errors in the measured parameters.

If the camera 100 includes the pattern generator 136, the pattern generator 136 is aligned with the camera 100 to illuminate the ulcer 300 to be captured by the camera 100. When the projected grid form pattern 138 illuminates the ulcer 300, the ulcer 300 will be within a viewing angle of the camera 100. For best results, particularly when multiple frames are to be captured, it is important that the camera be secured in its position for the duration of the image capture operation. This can be best accomplished using, for example, an articulating arm or tripod (not shown), which is commonly used for this purpose in photography.

The present invention provides for the quantitative measurement and interpretation of pressure sores. Furthermore, it provides a database of information pertaining to the patient and the patient's ulcer history. Thus, the effectiveness of a medical treatment procedure can be scientifically quantified.

Utilizing a single camera, and in conjunction with information about the distance from the camera to the ulcer, and information about the orientation of the ulcer, the present invention operates to derive measurements characterizing the ulcer. Image processing determines quantitative characteristics of the pressure ulcers, nevi and actinic-keratoses. Nevi are moles, which are round dome-shaped, smooth, or pimple-like, skin structures. They may be covered with a whitish dry crusty scale, which indicates overgrowth of the superficial layer of the skin (keratin). If the color is dark brown (or black), the ulcer may become mottled lesions or eruptions. Acne (an inflammation of hair glands on the face or trunk) can manifest itself as pustules or cysts. They may be pitted, depressed, or scar-like. Actinic-keratoses are dry freckle-like spots appearing on sun exposed skin areas. They may appear as single or multiple, dry, rough surfaced adherent scaly lesions, According to a variation of the present invention, color and color variability (called texture) is additionally examined to determine the severity of the ulcer. Color information helps to locate and assess the seriousness of the ulcer. Texture information helps identify the edge of the ulcer.

All of the above image-capture approaches, such as, the single image capturing, the stereoscopic, and the multi-image swath provide accurate color information, particularly in a light controlled environment of consistent spectral composition. A controlled light condition can be provided by artificial light, such as, but not limited to, for example, incandescent or flash light, which may optionally be attached to the camera 100 or other part of the system. While all approaches will capture texture information of the ulcer region, the single image capture approach will be the least effective and the multi-image swath approach will be the most effective.

One skilled in the art can see how the use of image data including simultaneous projected patterns, visible features and one or more recorded images can all be combined to provide a comprehensive interpretation of the physical condition and rate of progress of the ulcer treatment.

Further, it is understood that the present invention may provide multiple-frame images that are obtained by moving the projected image or camera (or both), in order to obtain additional image information that can be analyzed to determine the effectiveness of the ulcer treatment. Additionally, it is possible to capture multiple parts of a complete pattern in several images, which are then combined in the image processing software.

The above discussion deals with the objective and accurate characterization of the physical parameters of pressure ulcers. It is noted that while the invention has been described with respect to the treatment of ulcers, the invention described herein is equally suitable for the characterization of other dermatological subjects, such as, but not limited to, for example, moles, lesions, eruptions such as acne, and/or features such as, for example, scars or other blemishes.

As noted above, the present invention can be employed to process the image at the time that the image is captured. Alternatively, the present invention provides for the post-processing of the captured image at a later time. Further, the processing may be performed at the same location as where the image was captured, or at a location remote from the image capturing.

The foregoing discussion has been provided merely for the purpose of explanation and is in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims. The invention described herein comprise dedicated hardware implementations including, but not limited to, application specific integrated circuits, programmable logic arrays and other hardware devices constructed to implement the invention described herein. However, it is understood that alternative software implementations including, but not limited to, distributed processing or component/object distributed processing, parallel processing, or virtual machine processing can also be constructed to implement the invention described herein.

We claim:

1. An apparatus for at least one of measuring and characterizing a selected skin lesion, comprising:
   a capture device that produces data representing an image of an object;
   a processing device that processes said data to derive a three-dimensional model of the skin lesion that is stored in a database; and
   a reporting device that indicates at least one specific property of the selected skin lesion, wherein said processing device determines a change in said at least one specific property by comparing said three-dimensional model with at least one previously derived three-dimensional model stored in said database, wherein said data representing an image includes information related to at least one of color and texture of the object.

2. The apparatus of claim 1, wherein said capture device comprises an electronic stereoscopic camera.

3. The apparatus of claim 1, wherein said capture device comprises an electronic camera having at least one periscope.

4. The apparatus of claim 3, wherein said electronic camera captures at least two images on a split frame.

5. The apparatus of claim 1, wherein said capture device captures space diverse views of the object.

6. The apparatus of claim 1, wherein said capture device comprises a scanner.

7. The apparatus of claim 1, wherein said capture device comprises plural cameras.

8. The apparatus of claim 1, wherein said capture device further comprises a memory that stores said captured image.

9. The apparatus of claim 8, wherein said stored captured image is analyzed by said processing device at a time that is substantially later from when the image was captured.

10. The apparatus of claim 1, further comprising an interface that selectively connects said capture device to said processing device.

11. The apparatus of claim 1, wherein said reporting device comprises a display.

12. The apparatus of claim 1, wherein said data stored in said database is correlated with selected information.

13. The apparatus of claim 12, wherein said selected information comprises at least one of patient identification, lesion location, date said data representing said image of said object was produced, time said data representing said image of said object was produced, and identification of personnel treating said object.

14. The apparatus of claim 1, further comprising a pattern generator that projects a predetermined pattern onto said object.

15. The apparatus of claim 14, wherein said predetermined pattern comprises a grid pattern.

16. The apparatus of claim 14, wherein said predetermined pattern comprises a plurality of geometric shapes.

17. A method for at least one of measuring and characterizing a selected skin lesion, comprising:
    producing data that represents an image of an object;
    processing the data to derive a three-dimensional model of the skin lesion that is stored in a database; and
    indicating at least one specific property of the selected skin lesion, wherein a change in the at least one specific property is determined by comparing the three-dimensional model with at least one previously derived three-dimensional model stored in the database, wherein the data representing an image includes information related to at least one of color and texture of the object.

18. The method of claim 17, further comprising using an electronic stereoscopic camera to capture the image.

19. The method of claim 17, further comprising using an electronic camera having at least one periscope to capture the image.

20. The method of claim 19, further comprising capturing at least two images on a split frame of the electronic camera.

21. The method of claim 17, further comprising using a capture device that captures space diverse views of the object.

22. The method of claim 21, wherein the capture device further comprises storing the captured image in a memory.

23. The method of claim 22, further comprising processing the captured image stored in the memory at a time that is substantially later from when the image was captured.

24. The method of claim 17, wherein producing data that represents an image of an object comprises using a scanner.

25. The method of claim 17, further comprising using plural cameras to capture the image.

26. A method for at least one of measuring and characterizing features of an object, comprising:

transforming an initial image view to a two-dimensional physical perspective representation of an image corresponding to the object;

identifying unique features of the two-dimensional perspective representation of the image;

correlating the identified unique features to produce a three-dimensional physical representation of all uniquely-identified features; and determining three-dimensional characteristic features of the object, wherein the identified unique features include information related to at least one of color, and texture of the object.

27. The method of claim 26, further comprising using a capture device that produces the initial image view by capturing space diverse views of the object.

28. The method of claim 26, wherein the capture device further comprising storing the initial image view in a memory, associated with the capture device, for later retrieval.

29. An apparatus for at least one of measuring and characterizing features of an object, comprising:

an imaging device that captures a two-dimensional image of the object;

a processing device that processes said captured image to produce a three-dimensional representation of the object, said three-dimensional representation including parameters indicating a predetermined feature of the object;

a database that stores said parameters;

a comparing device that compares said stored parameters to previously stored parameters related to the object to determine a change in the three-dimensional representation of the object; and a reporting device that uses results of said comparison by said comparing device to generate a report pertaining to a change in the object, wherein said parameters indicating a predetermined feature of the object includes information related to at least one of color and texture of the object.

30. The apparatus of claim 29, further comprising a pattern generator that projects a predetermined pattern onto the object to assist in capturing said two-dimensional image of the object.

31. The apparatus of claim 29, further comprising an interface that selectively connects said imaging device to said processing device.

* * * * *